United States Patent [19]
Ohorodnik et al.

[11] 3,978,146
[45] Aug. 31, 1976

[54] PRODUCTION OF 2-CHLOROBUTADIENE-1,3

[75] Inventors: Alexander Ohorodnik, Erftstadt-Liblar; Udo Dettmeier, Okriftel; Klaus Gehrmann, Hurth-Knapsack; Heinz-Josef Berns, Hurth-Berrenrath, all of Germany

[73] Assignee: Hoechst Aktiengesellschaft, Frankfurt am Main, Germany

[22] Filed: Feb. 10, 1975

[21] Appl. No.: 548,420

Related U.S. Application Data

[63] Continuation of Ser. No. 277,853, Aug. 4, 1972, abandoned.

[30] Foreign Application Priority Data

Aug. 7, 1971  Germany............................. 2139729

[52] U.S. Cl. ............................................... 260/655
[51] Int. Cl.². ........................................ C07C 21/21
[58] Field of Search ..................................... 260/655

[56] References Cited
FOREIGN PATENTS OR APPLICATIONS 1,197,539   7/1970   United Kingdom................. 260/655

*Primary Examiner*—Delbert E. Gantz
*Assistant Examiner*—Joseph A. Boska
*Attorney, Agent, or Firm*—Connolly and Hutz

[57] ABSTRACT

Production of 2-chlorobutadiene-(1,3) by the dehydrochlorination of 3,4-dichlorobutene-(1) in an aqueous solution of an alkali metal or alkaline earth metal hydroxide in the presence of an alcohol having between 2 and 4 carbon atoms at elevated temperature, and distilling off resulting 2-chlorobutadiene-(1,3). To this end, a reaction zone is continuously supplied with 3,4-dichlorobutene-(1), an alcohol and the aqueous hydroxide solution and the whole is heated to boiling therein while passing a stream of inert gas therethrough; resulting 2-chlorobutadiene-(1,3) is distilled off from the reaction zone and fractionated until pure; a reaction mixture which commences to separate into two layers comprising an upper layer and a lower layer is retained in the reaction zone; aqueous alcohol in excess is continuously removed from said upper layer through an overflow and the alcohol is recovered; the lower layer consisting of an aqueous/alkaline solution of unreacted hydroxide, chloride salt and minor amounts of alcohol is continuously removed through the bottom of the reaction zone; the lower layer is distilled so as to concentrate it; precipitated chloride salt is isolated, and concentrated liquor is recovered.

8 Claims, 1 Drawing Figure

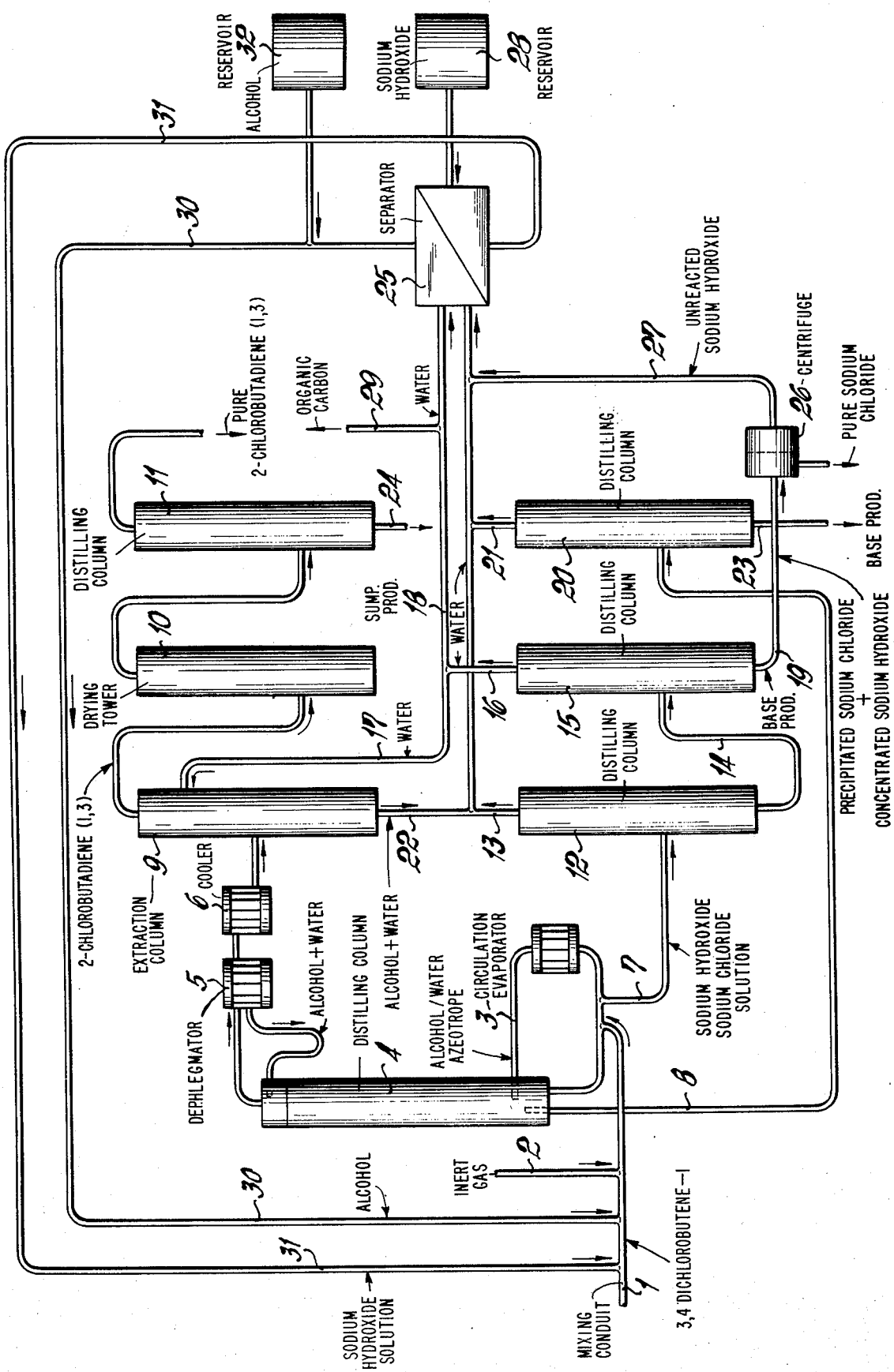

PRODUCTION OF 2-CHLOROBUTADIENE-1,3

This application is a continuation of application Ser. No. 277,853 filed Aug. 4, 1972 and now abandoned.

The present invention relates to a process for the manufacture of 2-chlorobutadiene-(1,3) comprising dehydrochlorinating 3,4-dichlorobutene-(1) in the aqueous solution of an alkali metal or alkaline earth metal hydroxide in the presence of an alcohol having between 2 and 4 carbon atoms at elevated temperature, and distilling off resulting 2-chlorobutadiene-(1,3).

Similar processes have already been described in German published specification DOS No. 1,814,075 and Japanese published specification No. 42-25054.

The process reported in German published specification DOS No. 1,814,075 is carried out batchwise at temperatures between 10° and 60°C and produces 2-chlorobutadiene-(1,3) in yields between 95 and 99.5%, based on 3,4-dichlorobutene-1. This process which comprises two separate processing steps subdivided into a reaction step and finishing step cannot be carried out continuously, which is disadvantageous.

As taught in Japanese published specification No. 42-25054, it is possible by semi-continuous operation at temperatures between 60° and 70°C which, however, does not provide for the circulation firstly of the alkali liquor in excess and secondly of the inert alcohols, to produce 2-chlorobutadiene-(1,3) in yields between 93 and 96 %. 2-Chlorobutadiene-1,3 produced at that temperature contains a 1-chlorobutadiene-1,3 by-product in a low concentration of at most 0.5 weight %. At 90°C, however, the by-product concentration is as high as about 1.7 weight percent.

Attempts are made in these two processes to improve the contact between the immiscible starting materials comprising 3,4-dichlorobutene-1 and aqueous alkali liquor, by the addition of an alcohol as an inert dissolving intermediary or solute so as to increase the reaction velocity.

These conventional processes are not fully satisfactory, however, as they can scarcely be carried out in continuous fashion and as it is impossible to take care therein of the changes which occur in the reaction medium, during the reaction. This is particularly true concerning the reaction mixture, which shows an increasing concentration of contaminants originating from the 3,4-dichlorobutene-1 feed material and of stabilizers, which may have been added thereto. These are readily soluble in alcohol but difficultly soluble in the aqueous phase of the reaction mixture and this means in the end that the desirable solubilizing effect is partially annulled. In addition to this, the contaminants have been found to impair firstly the quality of the excess of alkali liquor or alkaline earth liquor, which is to be recovered, and secondly the quality of the chloride salt, for example sodium chloride, which is obtained during the dehydrochlorination. On the other hand, it is apparently impossible by the use of an excess of alcohol to maintain the above contaminants in solution, in the absence of any disclosure in the above conventional processes how to effect the continuous removal of the alcohol in excess together with the dissolved contaminants from the reactor, and how to effect the work-up of these materials under commercially attractive conditions.

The present invention now provides a fully continuous one-step process for the manufacture of 2-chlorobutadiene-1,3 under commercially attractive conditions. In the process of the present invention, 2-chlorobutadiene-1,3 is obtained in yields between 95 and 99.5%, based on the 3,4-dichlorobutene-1 used, conditional upon the nature of the alcohol, and more than 99% of the 3,4-dichlorobutene-1 undergo conversion. The 2-chlorobutadiene-1,3 produced in accordance with this invention contains as little as between 0.5 and 0.6 weight percent of 1-chlorobutadiene-1,3 together with substantially between 0.01 and 0.03 weight % of acetaldehyde. In other words, it has the purity necessary for polymerization. A particularly beneficial effect of the process of the present invention resides in the fact that it is unnecessary to use very pure 3,4-dichlorobutene-1 therein, which may well be replaced by less expensive commercially pure (substantially 97–98%) 3,4-dichlorobutene-1 or by even less pure (93.6%) material, for continual operation without any losses in yield.

The process of the present invention comprises more particularly continuously supplying a reactive zone with 3,4-dichlorobutene-(1), an alcohol and the aqueous hydroxide solution and heating them to boiling therein while passing a stream of inert gas therethrough; distilling off from the reaction zone resulting 2-chlorobutadiene-(1,3) and fractionating it until pure; retaining in the reaction zone a reaction mixture which commences to separate into two layers comprising an upper layer and a lower layer; continuously removing aqueous alcohol in excess from said upper layer through an overflow and recovering the alcohol; continuously removing through the bottom of the reaction zone the said lower layer consisting of an aqueous/alkaline solution of unreacted hydroxide, chloride salt and minor proportions of alcohol; distilling the said lower layer so as to concentrate it; isolating precipitated chloride salt, and recovering concentrated liquor.

Further preferred features of the process of the present invention, which can be used singly or in combination, comprise:

a. maintaining the reaction zone at the boiling temperature of the respective alcohol/water-azeotrope;

b. maintaining a temperature between 70° and 95°C in the reaction zone;

c. effecting the reaction under pressures between 0.1 and 2 atmospheres absolute, preferably at atmospheric pressure;

d. initiating the reaction in the reaction zone by first supplying the alcohol and the aqueous hydroxide solution and then continuously adding a mixture of 3,4-dichlorobutene-(1), alcohol and aqueous hydroxide solution;

e. using a reaction mixture containing between 10 and 90, preferably between 40 and 60% by volume of alcohol, in the reaction zone;

f. using a sodium hydroxide solution with a strength between 8 and 24 weight % as the aqueous alkali metal hydroxide solution;

g. delivering from the reaction zone resulting 2-chlorobutadiene-(1,3) together with an alcohol/water-azeotrope and diluted with the inert gas passed through said zone to a first distilling zone; maintaining the said distilling zone at a head temperature which is at least 5°C lower than the boiling point (under the reaction conditions) of the alcohol/water-azeotrope, and distilling off in said first distilling zone the said 2-chlorobutadiene-(1,3) and the said azeotrope, the alcohol/water-azeotrope being selectively condensed and recycled to the reaction zone; condensing the resulting vaporous, crude and alcohol-containing 2-chlorobutadiene-(1,3) and introducing it into an extraction zone; scrubbing the 2-chlorobutadiene-(1,3) therein with water flowing countercurrently with respect thereto, drying it and fractionating it until pure;

h. establishing a temperature between 35°C and the boiling point of 2-chlorobutadiene-(1,3) (under the reaction conditions) at the head of the first distilling zone;

i. introducing the aqueous alcohol, which is continuously removed from the said upper layer of the reaction mixture through said overflow, into a second distilling zone and removing an alcohol/water-mixture overhead;

j. introducing the said lower aqueous/alkaline layer, which is removed through the bottom of the reaction zone, into a third distilling zone, distilling off an alcohol/water-mixture overhead and delivering base product, which is obtained in said third distilling zone, to a fourth distilling zone, distilling off water therein and thereby transforming the said base product into a concentrated liquor containing precipitated chloride salt; filtering or centrifuging the said concentrated liquor so as to recover pure chloride salt and pure concentrated liquor;

k. recycling a portion of the distilled water, which is obtained in the fourth distilling zone, to the extraction zone for use as scrubbing water therein, delivering a further portion of said water to a separating zone, and rejecting the balance portion of said water, which is easy to degrade biologically; removing scrubbing water containing alcohol through the bottom of the extraction zone and introducing the said scrubbing water together with the alcohol/water-mixtures which are distilled off at the head of the said second and third distilling zones, respectively, into the separation zone; replacing spent hydroxide in the separation zone by the introduction of the necessary quantity of concentrated liquor thereinto with the resultant formation of an upper layer rich in alcohol and a lower aqueous/alkaline layer of desirable concentration; separating the said upper and the said lower layers from one another and continuously recycling to the reaction zone the said separate layers together with fresh 3,4-dichlorobutene-(1) and together with the quantity of fresh alcohol needed to replace the quantity of alcohol consumed during one passage cycle;

l. using a circulation evaporator as the reaction zone.

The useful $C_2$–$C_4$-alcohols include n-propanol, ethanol, isopropanol, n-, iso-, sec. and tert. butanol (cf. Example 5), n-propanol being preferred. The boiling temperatures of the respective alcohol/water-azeotropes, which are established in the reaction zone, are between 78° and 93°C at atmospheric pressure. Higher or lower temperatures are a function of the reaction pressure selected. The reaction of this invention should preferably be carried out with the use of n-propanol and water and at the boiling temperature of the corresponding azeotrope of 87°C (under a pressure of 760 mm Hg). Despite the high reaction temperatures, the dehydrochlorination is highly selective and takes place without any appreciable formation of by-products. Full use can therefore be made of the increased reaction velocity in the dehydrochlorination reaction, at the boiling points of the alcohol/water-azeotropes.

The useful hydroxides include sodium hydroxide, potassium hydroxide or calcium hydroxide in aqueous solutions (liquors), sodium hydroxide being preferred. The yield and conversion rate substantially do not depend on the concentration of these liquors, in the present process. Speaking generally, sufficient water should normally be used so as to maintain the resulting chloride salt, e.g. NaCl, in solution. This in view of the fact that salt, if it ever precipitates, may obstruct the circulation evaporator and conduits. On the other hand, it is good practice to use a fairly small quantity of water, with a view to reasonable dimensions of the reactor. The reaction carried out in the presence of n-propanol and, for example, with the use of a sodium hydroxide solution having a strength of 22 weight % could not be found to entail the precipitation of NaCl. NaCl commences, however, to precipitate if use is made of a sodium hydroxide solution with a strength of 25 weight % (cf. Example 3). The dehydrochlorination should accordingly and preferably be carried out with the use of a sodium hydroxide solution with a strength between 8 and 24 weight %, more preferably 22 weight %.

While the molar ratios in which the hydroxide, for example NaOH, KOH or $Ca(OH)_2$ and the 3,4-dichlorobutene-1 are used may vary within wide limits, it is generally preferred to use between 1 and 2 mols, advantageously between 1.1 and 1.3 mols, of hydroxide per mol of 3,4-dichlorobutene-1, so as to avoid uneconomic use of an excess of hydroxide.

The step of circulating the alcohol and the hydroxide in excess and the step of recovering the resulting chloride salt are critical for the process of the present invention. It should be added that purified effluent water is simultaneously obtained therein, the removal of which is no problem. This is a further important aspect for the commercialization of the present process. These are four features vital to the economy of the present process.

A preferred method of carrying out the process of the present invention will now be described with reference to the accompanying drawing.

3,4-Dichlorobutene-1 is mixed continuously in mixing conduit 1 with sodium hydroxide solution travelling through conduit 31, with alcohol travelling through conduit 30, and with an inert propellent gas, preferably nitrogen, flowing through conduit 2, and the resulting mixture is introduced into circulation evaporator 3 (reaction zone), which is preferably charged previously, i.e. prior to starting the continuous operation, with a boiling mixture of alcohol/sodium hydroxide solution. The reaction commences at once and the resulting 2-chlorobutadiene-1,3, which is diluted with nitrogen and the azeotropically boiling alcohol/water-mixture, is distilled in distilling column 4, the dephlegmator of which is maintained at a temperature at least 5°C lower than the boiling point of the alcohol/water-azeotrope. This is done to effect condensation of the bulk of the alcohol/water-mixture in dephlegmator 5 and recycle it to the head of distilling column 4. Crude 2-chlorobutadiene-1,3, which is distilled off continuously, is condensed in cooler 6, then conveyed to extraction column 9 and freed therein from dissolved alcohol by scrubbing with water travelling through conduit 17. Alcohol-containing scrubbing water is removed through the bottom of column 9, through conduit 22. Following this, the 2-chlorobutadiene-1,3 is dried in conventional manner in drying tower 10, for example by treatment with $CaCl_2$, and fractionated in distilling column 11 until pure. The sump product which accumulates in the base portion of distilling column 11 is discharged through line 24 and rejected.

The dehydrochlorination reaction in circulation evaporator 3 is effected in a two phase-system comprising an aqueous sodium hydroxide/alcohol-solution and a specifically heavier aqueous sodium hydroxide/sodium chloride-solution.

Owing to the high concentration of salt in the aqueous sodium hydroxide solution, it is only natural that the alcohol has a minor solubility only in the aqueous phase; between 1 and 10 weight % are normally soluble therein, conditional upon the concentration of the sodium hydroxide solution and the chain length of the alcohol. The sodium hydroxide/alcohol-phase contains between 0.5 and 1 weight % of sodium hydroxide.

A portion of the specifically lighter aqueous sodium hydroxide/alcohol-phase, which is circulated, flows continously through overflow conduit 8. In other words, a given liquids level is maintained in circulation evaporator 3 and in the bottom portion of distilling column 4. The sodium hydroxide/alcohol-phase in excess, which flows through conduit 8, is distilled in distilling column 20, and an alcohol/water-mixture is distilled off through conduit 21. The base product of distilling column 20 is removed through conduit 23 and rejected.

A portion of the non-circulated specifically heavier aqueous sodium hydroxide/sodium chloride-solution is continuously removed through the bottom of circulation evaporator 3 through conduit 7, delivered to distilling column 12, distilled therein, and an alcohol/water-mixture is removed overhead, through conduit 13. The base product accumulating in column 12 is conveyed through conduit 14 to distilling column 15 and further concentrated therein. A portion of the water, which is distilled off through conduit 16, is recycled through conduit 17 to extraction column 9 for use as scrubbing water therein, and a further portion is introduced into separator 25, through conduit 18. The balance portion of the water, which is easy to degrade biologically and contains less than 0.1 weight % of organic carbon, is removed through branch line 29. The base product accumulating in distilling column 15 is a suspension of precipitated sodium chloride in concentrated sodium hydroxide solution. It is removed through conduit 9 and delivered to a filtration apparatus or centrifuge 26, in which solid sodium chloride with a purity of more than 99.5% and suitable for use in the electrolysis of alkali chlorides, for example, is continuously obtained. The filtrate, which contains unreacted sodium hydroxide, is a concentrated sodium hydroxide solution (45–55 weight %) containing as little as between 1 and 3 weight % of sodium chloride. It is introduced into separator 25, through conduit 27.

The alcohol-containing scrubbing water flowing through conduit 22 is also introduced continuously and together with the alcohol/water-mixtures travelling through head conduits 13 and 21, respectively, into separator 25.

Separator 25 receives a calculated amount of fresh concentrated sodium hydroxide solution coming from reservoir 28. This results in the formation of two phases which are separated from one another, namely an upper phase layer consisting substantially of alcohol with little water therein. Following replacement of the slight losses of alcohol by alcohol coming from reservoir 32, the upper phase layer is continuously recycled to circulation evaporator 3, through conduits 30 and 1. Less than 5% of the alcohol circulated is lost. The lower phase layer formed in separator 25 consists of sodium hydroxide solution of desirable concentration, and is continuously recycled to circulation evaporator 3, through conduits 31 and 1.

It is also possible to carry out the finishing treatment in the following manner:

1. The materials travelling through conduits 8 and 22, respectively, are united in a mixing tube connected to a separator with the resultant formation of two phases, of which the specifically heavier aqueous phase is introduced into separator 25 and used therein for the preparation of fresh sodium hydroxide solution, and of which the specifically lighter oily phase is discarded. This is not fully satisfactory, however, as traces of organic contaminants originating from the oil may impair the quality of the sodium hydroxide solution.

2. The materials travelling through conduits 7 and 8, respectively, are united, the resulting oil is separated and discarded, and the aqueous phase is worked up in distilling column 12. This is not fully satisfactory as less pure sodium chloride is obtained.

3. Separator 25 may be omitted provided that the quantities of alcohol and sodium hydroxide solution needed in circulation evaporator 3 are directly recycled to mixing conduit 1, the alcohol travelling through conduits 22, 13 and 16, and the sodium hydroxide solution travelling through conduit 27.

4. The distillate obtained in conduit 21 is directly introduced into conduit 30.

While the finishing treatment described under (3) and (4) above is substantially free from disadvantages, use should preferably be made of the finishing treatment first described herein, which enables more accurate control to be made of the quantities of alcohol to be added and of the concentration of the sodium hydroxide solution to be used.

The following statements are intended further to illustrate the process of the present invention.

While the dehydrochlorination should preferably be effected in a circulation evaporator, it is possible to use for continuous operation a pulsator, vibrator or agitator, for example, provided that they enable the reactants in the reactor to be thoroughly mixed together.

The reaction mixture in the reaction zone should conveniently contain at least 10 and at most 90% by volume of alcohol. If use were made of less than 10%, the reaction mixture would commence foaming, and if use were made of more than 90%, the reaction velocity would be considerably reduced. In these extreme cases losses in yield would be inevitable.

The use of overflow conduit 8 is particularly critical for continuous operation. Conduit 8 enables use to be made of any desirable quantity of alcohol as the maintenance of a constant reactor volume and the continuous removal of alcohol in excess are warranted. Circulation evaporator 3, which is supplied continuously with alcohol, should preferably receive the quantity of alcohol which is necessary to at least compensate the quantity of alcohol discharged with the distillate coming from distilling column 4 and travelling through conduits 7 and 8. As compared with prior art processes, this is very advantageous as contaminants (including, for example, stabilizer residues; dimers and polymers of 2-chlorobutadiene-1,3; 1,4-dichlorobutene-2 and higher-boiling trichlorobutenes which accompany the 3,4-dichlorobutene-1 feed material) which may be found to concentrate upon prolonged operation and to reduce the reaction velocity, are dissolved in the alcoholic phase and therefore easy to remove continuously from the reaction mixture. The alcoholic phase removed through overflow conduit 8 contains little aqueous liquor together with merely traces of 2-chlorobutadiene-1,3. As can be seen from comparative Example 4 below (this Example was carried out without the use of overflow conduit 8, i.e. substantially in accordance with the art), continuous operation was disturbed by accumulating contaminants which impaired the yield, and this despite the use of 99.9% pure 3,4-dichlorobutene-1 therein.

The first distilling zone may comprise, for example, distilling column 4 having a dephlegmator 5 or a heated column section mounted thereon. Under the pressure conditions selected, the temperature near the head of the first distilling zone or in dephlegmator 5 should preferably be lower than the boiling point of 2-chlorobutadiene-1,3, for example lower than 59.4°C under a pressure of 760 mm of Hg. This in view of the fact that 2-chlorobutadiene-1,3 diluted with the inert gas, for example with the nitrogen propellent, is already volatile at temperatures which are lower than its boiling point. Dephlegmator 5 should therefore be maintained at preferred temperatures between 35° and 50°C, under atmospheric pressure. It is possible in this manner substantially to avoid undesirable distillation of the alcohol/water-azeotrope in first distilling column (4;5) and to maintain constant volume relations in the reaction zone. If use is made of n-propanol, for example, then the crude 2-chlorobutadiene-1,3 obtained in cooler 6 merely contains between 1 and 5 weight % of n-propanol. If use is made of ethanol or isopropanol, the alcohol concentration is found to increase up to 10–18 weight %. The reflux ratio in distilling column 4 may be selected within the limits of 3:1 to 5:1. To stabilize the resulting 2-chlorobutadiene-1,3, it is good practice to mix the reaction mixture with a minor proportion of a stabilizer, for example phenothiazine and/or n-nitrosodiphenylamine.

EXAMPLE 1

23 Liters (18.4 kg) of n-propanol (100%) and 12 liters (14.8 kg) of sodium hydroxide solution with a strength of 22 weight % were introduced into a steam-heated circulation evaporator 3. The n-propanol was stabilized with 0.2 weight % of phenothiazine and 0.1 weight % of N-nitrosodiphenylamine. A slight stream (30 normal liters/hr, measured at STP) of nitrogen was introduced into circulation evaporator 3, through conduits 2 and 1. The mixture was heated to boiling at 87°C and mixing conduit 1 was used to add thereto, per hour, 5.06 liters (5.84 kg) of crude 3,4-dichlorobutene-1 (93.6 weight % of 3,4-dichlorobutene-1; 4.8 weight % of 1,4-dichlorobutene-2; 0.4 weight % of low-boiling (< 59.4°C) and 1.2 weight % of higher-boiling (> 155°C) contaminants), 8.88 liters (10.92 kg) of sodium hydroxide solution with a strength of 21.8 weight % (coming from conduit 31) and 1.32 liters (1.11 kg) of n-propanol, which contained 12 weight % of water and came from conduit 30. The reaction mixture contained an average quantity of substantially 48% by volume of n-propanol.

The resulting 2-chlorobutadiene-1,3 ($bp_{760}$=59.4°C) was distilled off at the same rate as it was formed, from distilling column 4. The temperature prevailing in dephlegmator 5 was 45°C. In cooler 6, there were obtained, per hour, 4.2 liters (3.93 kg) of crude 2-chlorobutadiene-1,3 (97.7 weight % of 2-chlorobutadiene-1,3; 1.4 weight % of n-propanol; 0.5 weight % of 1-chlorobutadiene-1,3; the balance being contaminants) which was introduced into extraction column 9, scrubbed therein until free from propanol with 3.14 liters/hr of water coming from conduit 17, dried with $CaCl_2$ in drying tower 10 and fractionated until pure in distilling column 11. 4.11 liters (3.82 kg) of 2-chlorobutadiene-1,3 were obtained per hour. After 24 hours of dehydrochlorination, crude 2-chlorobutadiene-1,3 was obtained in a yield of 99.2%, based on the 3,4-dichlorobutene-1 used. The yield remained unchanged during continuous operation over 7 days. Pure 2-chlorobutadiene-1,3 was obtained in distilling column 11 in a yield of 98.0%.

10.5 Liters/hr of non-circulated aqueous phase (20.6 weight % of NaCl; 4.9 weight % of NaOH; 1.9 weight % of n-propanol; 72.6 weight % of water) were removed from evaporator 3 through conduit 7 and distilled in distilling column 12. 1.2 Liters of distillate were removed per hour through head conduit 13 (81.9 weight % of water; 18.1 weight % of propanol). The base product (9.3 liters) was introduced through conduit 14 into distilling column 15 and concentrated therein so as to obtain a thick liquor containing 48.5 weight % of NaOH and 2.8 weight % of dissolved NaCl; 2.56 kg of NaCl were found to have been precipitated. This mixture was discharged through conduit 19, the precipitated NaCl was filtered off in filter 26 and the filtrate (0.71 liter=1.07 kg) was delivered to separator 25, through conduit 27.

The distillate obtained in column 15, of which more than 99.9% were water, was removed through conduit 16 and condensed (7.51 liters/hr). 3.14 Liters/hr were introduced into conduit 17 and the balance was removed through conduit 18. More particularly, 1.76 liters/hr were introduced into separator 25 and used for the preparation of fresh sodium hydroxide solution therein, whilst 2.61 liters/hr were effluent water, which contained less than 0.1 weight % of residual carbon, were discarded, through conduit 29.

1.02 Liters/hr of organic phase (72.9 weight % of n-propanol; 11.3 weight % of $H_2O$; 0.97 weight % of NaOH; 3.2 weight % of 2-chlorobutadiene-1,3; 11.6 weight % of higher boiling contaminants (> 100°C) left the bottom zone of distilling column 4 through overflow conduit 8 and were distilled in distilling column 20. 0.94 Liter/hr (= 0.80 kg) of a n-propanol/water-mixture (74.8 weight % of n-propanol; 12.43 weight % of $H_2O$; 3.2 weight % of 2-chlorobutadiene-1,3, the balance being contaminants) was found to distil off through head conduit 21. The mixture was united firstly with 3.14 liters/hr of scrubbing water (98.0 weight % of $H_2O$; 2.0 weight % of n-propanol) coming from conduit 22 and secondly with the 1.2 liters/hr of distillate travelling through head conduit 13, and the whole was introduced into separator 25. Separator 25 was further fed with 2.79 liters/hr (4.13 kg/hr) of sodium hydroxide solution (45 weight % strength) coming from container 28. This resulted in the formation of two phases.

The upper phase (1.28 liters/hr = 1.08 kg/hr) consisted of 87 weight % of n-propanol and 13 weight % of water and was recycled to reaction zone 3, through conduit 30. 3.8% of pure n-propanol, based on the quantity of n-propanol initially added (1.32 liters/hr = 1.11 kg/hr of n-propanol with a strength of 88 weight %) were lost. The loss was compensated by the addition of 45 ml/hr (= 36 grams/hr) of n-propanol of 100 weight % strength, coming from reservoir 32.

The lower phase (8.88 liters/hr = 10.92 kg/hr) was a sodium hydroxide solution with a strength of 21.8 weight %. It was recycled to reaction zone 3 through conduit 31.

EXAMPLE 2

The procedure described in Example 1 was repeated with the use of the same quantities of n-propanol save firstly that the sodium hydroxide solution first introduced into the reaction zone and that which was continuously added later contained as little as 10 weight % of NaOH, and secondly that merely 2.32 liters/hr (=2.68 kg/hr) of crude 3,4-dichlorobutene-1 were added. As a result, substantially 54% less 2-chlorobutadiene-1,3 was produced within the same period of time, for a constant molar ratio of 3,4-dichlorobutene-1 to NaOH. Crude 2-chlorobutadiene-1,3 was obtained in a yield of 99.3%, based on the 3,4-dichlorobutene-1 used.

EXAMPLE 3 (Comparative Example)

The procedure described in Example 1 was repeated with the use of the same amounts of n-propanol save firstly that the sodium hydroxide solution first introduced into the reaction zone and that which was continuously added later contained 25 weight % of NaOH. 5.80 Liters/hr (=6.7 kg/hr) of 3,4-dichlorobutene-1 were added at the same time. In other words, the molar ratio of 3,4-dichlorobutene-1 to NaOH was maintained constant. After 3 hours of operation, sodium chloride crystals which obstructed the aqueous phase outlet 7, commenced forming in circulation evaporator 3. This made it necessary to interrupt the dehydrochlorination reaction.

EXAMPLE 4 (Comparative Example)

The procedure described in Example 1 was repeated using the same apparatus save that overflow conduit 8 was omitted therein. It was necessary drastically to reduce the quantity of n-propanol added per hour and to limit the n-propanol addition to the quantity which was necessary to compensate the proportion of propanol removed from the reaction zone, through dephlegmator 5 and conduit 7.

Conduit 1 was used to supply evaporator 3, per hour, with 4.8 liters (5.5 kg) of 3,4-dichlorobutene-1 (purity: > 99.9%), 0.3 liter (250 grams) of n-propanol (85.8 weight % of n-propanol; 1.25 weight % of NaOH and 21.98 weight % of water) and 8.88 liters (10.92 kg) of sodium hydroxide solution with a strength of 21.8 weight %. After a reaction period of 4 hours, crude 2-chlorobutadiene-1,3 was obtained in a yield of 99.3%, based on the 3,4-dichlorobutene-1 used. The yield was 98.4%, after 8 hours: 98.1%, after 24 hours; 96.7%, after 48 hours; 93.6%, after 3 days; and 87.6%, after 4 days. After this time, an oily phase was found to have been formed on the surface of the reaction zone. The phase substantially consisted of higher-boiling contaminants (> 155°C), n-propanol and 3,4-dichlorobutene-1. In other words, the 3,4-dichlorobutene-1 added was found to merely partially react with the sodium hydroxide solution which was first introduced into the reactor.

EXAMPLE 5

The procedure described in Example 1 was repeated save that $C_2$–$C_4$-alcohols were substituted for the n-propanol. The boiling points of the respective alcohol/water-azeotropes, which were identical with the reaction temperatures used in the reaction zone, are indicated in the following Table, which also indicates the yields of crude 2-chlorobutadiene-1,3 obtained, based on the 3,4-dichlorobutene-1 used.

| Alcohol used | Bp in °C (760 mm Hg) | Bp of alcohol/ water-azeotrope in °C (760 mm Hg) | Yield of 2-chlorobutadiene-1,3 in %, based on the theoretical |
|---|---|---|---|
| ethanol | 78.3 | 78.2 | 98.0 |
| iso-propanol | 82.3 | 80.0 | 99.4 |
| (n-propanol | 97.2 | 87.0 | 99.2) |
| tert. butanol | 82.9 | 80.0 | 96.3 |
| sec. butanol | 99.5 | 87.5 | 95.6 |
| iso-butanol | 108.0 | 90.0 | 99.5 |
| n-butanol | 117.9 | 93.0 | 94.4 |

We claim:
1. A process for the manufacture of 2-chlorobutadiene-(1,3) by the dehydrochlorination of 3,4-dichlorobutene-(1) in an aqueous solution of an alkali metal or alkaline earth metal hydroxide in the presence of an alcohol having 2–4 carbon atoms at elevated temperature, and distilling off resulting 2-chlorobutadiene-(1,3), which comprises continuously supplying the lower part of a circulation reaction zone with 3,4-dichlorobutene-(1), an alcohol and the aqueous hydroxide solution, the resulting reaction mixture containing between 10 and 90% by volume of alcohol, and heating the mixture to boiling therein; continuously delivering from the reaction zone resulting 2-chlorobutadiene-(1,3) together with an alcohol/water-azeotrope to a first distilling zone comprising a dephlegmatory zone; maintaining the said dephlegmatory zone at a temperature between 35°C. and 50°C., and continuously distilling off in said first distilling zone the said 2-chlorobutadiene-(1,3) and the said azeotrope, the alcohol/water-azeotrope being selectively condensed and recycled to said first distilling zone; condensing the resulting vaporous, crude and alcohol-containing 2-chlorobutadiene-(1,3) and introducing it into an extraction zone; scrubbing the 2-chlorobutadiene-(1,3) therein with water flowing countercurrently with respect thereto, drying it and fractionating it until pure; retaining in the reaction zone a reaction mixture which separates into an upper layer and a lower layer; continuously removing an aqueous hydroxide/alcohol solution in excess from said upper layer through an overflow and recovering the alcohol; continuously removing through the bottom of the reaction zone a part of the said lower layer consisting of an aqueous alkaline solution of unreacted hydroxide, chloride salt and minor proportions of alcohol; distilling the removed part of the lower layer so as to concentrate it; isolating precipitated chloride salt, and recovering concentrated liquor.

2. The process as claimed in claim 1, wherein the reaction zone is maintained at the boiling temperature of the respective alcohol/water-azeotrope.

3. The process as claimed in claim 1, wherein a temperature between 70° and 95°C is maintained in the reaction zone.

4. The process as claimed in claim 1, wherein the reaction in the reaction zone is initiated by first supplying the alcohol and the aqueous hydroxide solution and then continuously adding a mixture of 3,4-dichlorobutene-(1), alcohol and aqueous hydroxide solution.

5. The process as claimed in claim 1, wherein a sodium hydroxide solution with a strength between 8 and 24 weight % is the aqueous alkali metal-hydroxide solution.

6. The process as claimed in claim 1, which comprises introducing the said part of the lower layer consisting of an aqueous alkaline solution of unreacted hydroxide, chloride salt and minor proportions of alcohol, which is removed through the bottom of the reaction zone, into a third distilling zone, distilling off an alcohol/water-mixture overhead and delivering base product, which is obtained in said third distilling zone, to a fourth distilling zone, distilling off water therein and thereby transforming the said base product into a concentrated liquor containing precipitated chloride salt; filtering or centrifuging the said concentrated liquor so as to recover pure chloride salt and pure concentrated liquor therefrom.

7. The process as claimed in claim 1, wherein the aqueous hydroxide/alcohol solution, which is continuously removed from the said upper layer of the reaction mixture through said overflow, is introduced into a second distilling zone and an alcohol/water-mixture is removed overhead of said second distilling zone.

8. The process as claimed in claim 1, which comprises introducing the aqueous hydroxide/alcohol solution, which is continuously removed from the said upper layer of the reaction mixture through said overflow, into a second distilling zone and removing an alcohol/water-mixture overhead of said second distilling zone; introducing the said part of the lower layer consisting of an aqueous alkaline solution of unreacted hydroxide, chloride salt and minor proportions of alcohol, which is removed through the bottom of the reaction zone, into a third distilling zone, distilling off an alcohol/water-mixture overhead and delivering base product, which is obtained in said third distilling zone, to a fourth distilling zone, distilling off water therein and thereby transforming the said base product into a concentrated liquor containing precipitated chloride salt; filtering or centrifuging the said concentrated liquor so as to recover pure chloride salt and pure concentrated liquor therefrom; recycling a portion of the distilled water, which is obtained in the fourth distilling zone, to the extraction zone for use as scrubbing water therein, delivering a further portion of said water to a separation zone, and rejecting the balance portion of said water, which is easy to degrade biologically; removing scrubbing water containing alcohol through the bottom of the extraction zone and introducing the said scrubbing water together with the alcohol/water-mixtures which are distilled off at the head of the said second and third distilling zones, respectively, into the separation zone; introducing thereinto the quantity of pure concentrated liquor necessary to replace spent hydroxide, with the resultant formation of an upper layer rich in alcohol and a lower aqueous alkaline layer of desirable concentration; separating the said upper and the said lower layers from one another and continuously recycling to the reaction zone the said separate layers together with fresh 3,4-dichlorobutene-(1) and together with the quantity of fresh alcohol needed to replace the quantity of alcohol lost during one passage cycle.

* * * * *